United States Patent
Bischoff et al.

(10) Patent No.: US 9,168,492 B2
(45) Date of Patent: Oct. 27, 2015

(54) ELEMENTS FOR SEPARATING SUBSTANCES BY DISTRIBUTING BETWEEN A STATIONARY AND A MOBILE PHASE, AND METHOD FOR THE PRODUCTION OF A SEPARATING DEVICE

(75) Inventors: Klaus Bischoff, Leonberg (DE); Sz Nyiredy, Budapest (HU); Klara Nyiredy-Mikita, legal representative, Budapest (HU); Zoltan Szuecs, Szentendre (HU)

(73) Assignee: BISCHOFF ANALYSENTECHNIK UND-GERAETE GMBH, Leonberg (DE)

( * ) Notice: Subject to any disclaimer, the term of this patent is extended or adjusted under 35 U.S.C. 154(b) by 1863 days.

(21) Appl. No.: 11/920,949

(22) PCT Filed: May 18, 2006

(86) PCT No.: PCT/EP2006/004744

§ 371 (c)(1),
(2), (4) Date: Mar. 31, 2010

(87) PCT Pub. No.: WO2006/125564

PCT Pub. Date: Nov. 30, 2006

(65) Prior Publication Data

US 2010/0213112 A1    Aug. 26, 2010

(30) Foreign Application Priority Data

May 23, 2005 (DE) .......................... 10 2005 024 154

(51) Int. Cl.
*B01D 57/02* (2006.01)
*B01D 15/22* (2006.01)
(Continued)

(52) U.S. Cl.
CPC ................ *B01D 57/02* (2013.01); *B01D 15/22* (2013.01); *G01N 30/6039* (2013.01);
(Continued)

(58) Field of Classification Search
CPC .... B01D 15/22; B01D 15/362; B01D 15/363; B01D 57/02; B01D 15/3804; G01N 30/6039; G01N 30/6069; G01N 30/6091; G01N 30/6004
USPC ............ 210/635, 656, 198.2, 232, 238, 502.1
See application file for complete search history.

(56) References Cited

U.S. PATENT DOCUMENTS 2,985,589 A    5/1961    Broughton et al.
3,763,879 A *  10/1973   Jaworek ..................... 137/268
(Continued)

FOREIGN PATENT DOCUMENTS

DE    1 130 204 B     5/1962
DE    38 36 343 A1    6/1989
(Continued)

OTHER PUBLICATIONS

PTO Translation No. 12-4534 of DE 1130204 Jun. 2012.*
(Continued)

*Primary Examiner* — Ernest G Therkorn
(74) *Attorney, Agent, or Firm* — Kriegsman & Kriegsman (57) ABSTRACT

The invention relates to elements for separating substances by distributing between a stationary and a mobile phase. Said separating elements comprise any stationary phase and a support element. The separating elements are part of a set that is provided with at least two separating elements $T_i$ (i=2) encompassing different stationary phases $S_i$ (i=2). The set comprises at least three pieces of each type of separating element $T_i$ with a specific stationary phase $S_i$. The separating elements can be coupled to each other or interconnected in another manner so as to form a separating device. The invention further relates to a method for producing an optimized device for separating substance mixtures.

7 Claims, 6 Drawing Sheets

(51) Int. Cl.
  *G01N 30/60* (2006.01)
  *B01D 15/36* (2006.01)
  *B01D 15/38* (2006.01)

(52) U.S. Cl.
  CPC ....... *G01N 30/6069* (2013.01); *G01N 30/6091* (2013.01); *B01D 15/362* (2013.01); *B01D 15/363* (2013.01); *B01D 15/3804* (2013.01); *G01N 30/6004* (2013.01)

(56) References Cited

U.S. PATENT DOCUMENTS

| | | | | |
|---|---|---|---|---|
| 4,301,139 A | * | 11/1981 | Feingers et al. | 436/500 |
| 4,550,594 A | * | 11/1985 | Engstrom | 73/61.53 |
| 4,719,011 A | * | 1/1988 | Shalon et al. | 210/198.2 |
| 4,740,306 A | * | 4/1988 | Litwack et al. | 210/198.2 |
| 4,787,971 A | * | 11/1988 | Donald | 210/198.2 |
| 6,541,273 B1 | * | 4/2003 | Plaisance | 436/178 |
| 2003/0010716 A1 | * | 1/2003 | Wankat | 210/638 |
| 2006/0118471 A1 | * | 6/2006 | Vidalinc | 210/198.2 |
| 2006/0186029 A1 | * | 8/2006 | Granger et al. | 210/198.2 |
| 2006/0207939 A1 | * | 9/2006 | Allington et al. | 210/656 |
| 2007/0240777 A1 | * | 10/2007 | Sasano et al. | 137/801 |
| 2009/0230045 A1 | * | 9/2009 | Kaneko et al. | 210/198.2 |

FOREIGN PATENT DOCUMENTS

| | | | |
|---|---|---|---|
| GB | 2212738 | * | 8/1989 |
| JP | 9072890 A | | 3/1997 |

OTHER PUBLICATIONS

PTO Translation No. 12-4565 of JP 09072890 Jun. 2012.*

* cited by examiner

ELEMENTS FOR SEPARATING SUBSTANCES BY DISTRIBUTING BETWEEN A STATIONARY AND A MOBILE PHASE, AND METHOD FOR THE PRODUCTION OF A SEPARATING DEVICE

REFERENCE TO RELATED APPLICATIONS

This application is a 371 of PCT/EP2006/004744 filed May 18, 2006.

The present invention relates to elements for separating substances by distributing between a stationary and a mobile phase, in particular for chromatography, and a method of production of the separating device comprising the stationary phase, in particular a chromatographic column.

Chromatography is a physicochemical method of separation, in which the substances to be separated are distributed between two phases, one of which, the stationary phase, is fixed, whereas the other, mobile phase moves in a defined direction.

The stationary phase is one of the two phases comprising the chromatographic system. A solid phase (sorbent), a liquid phase (solvent) or a gel can be used as the stationary phase. In the case of the liquid phase, this is applied to a solid (support), which may also be involved in the separating process. In the case of a bound phase, the layer with separating properties is bound chemically to a support or to the inside surface of a capillary.

Within the scope of the present invention, the stationary phases also include the quasistationary phases in liquid-liquid chromatography.

In order to protect the separating column against contaminants during chromatographic separation, the separating column is sometimes preceded by a precolumn.

In general the precolumn is filled with the same stationary phase as the separating column, or a material with lower retention is used.

In isocratic analysis the composition of the mobile phase remains constant throughout the elution operation.

In contrast, in gradient elution, the composition of the mobile phase is varied continuously or alternatively stepwise (step gradient).

In practice, substances of different polarities are often separated chromatographically over a wide range of polarity by gradient elution, as selective separation can be achieved in this way. In this case, a more polar mobile phase is added continuously or stepwise to an initially usually nonpolar mobile phase (normal-phase chromatography) or a less polar mobile phase is added to one that is more polar (reversed-phase chromatography).

For formation of the mobile phase by means of a gradient, chromatographs are required for gradient elution with at least two pumps for the different solvents or at least one low-pressure mixer and control software. The robustness of gradient separation is always poorer than that of isocratic separation.

Another disadvantage of gradient elution is that after elution with e.g. an increasingly more polar solvent mixture, the chromatographic system must be brought back again to the initial thermodynamic equilibrium with respect to the initially nonpolar mobile phase in the next elution, namely by extensive rinsing with the, in this example, nonpolar phase, before the column can be used for the next gradient elution. This "backwashing" is generally carried out with fifteen to twenty times the column volume and leads to a prolongation of the total cycle time and a considerable consumption of solvents.

Thus, separation of a large number of samples that are to be verified and separated by gradient elution, for example in quality control, has the disadvantage of the prolonged total cycle time, whereas for routine investigations of a large number of samples, the time per analysis with good separation should of course be as short as possible for economic reasons.

A further disadvantage of gradient elution is that the varying composition of the mobile phase means that certain detection principles cannot be employed. For example, the use of detectors based on measurement of refractive index is essentially ruled out when the composition of the mobile phase varies.

Even the UV/VIS detectors that are generally used are greatly restricted in their range of application in gradient elution on account of many admixed solvents and additives, e.g. methanol, THF, TFA, formic acid, acetic acid etc., which are themselves strongly absorbing in the UV range<230 nm.

Even with mass spectrometers, which have been used as universal detectors in recent times, secondary effects occur in gradient elution, e.g. problems of ionization in different chemical environments, making quantitative analysis much more difficult.

There are also ecological disadvantages in separation of substances by gradient elution: the mobile phase contained in a mixture after elution can only be recycled with difficulty, if at all, necessitating expensive disposal of the solvent mixture and additional costs for supply of the (fresh) solvents for forming the gradient. Moreover, gradient elution requires the use of far more expensive solvents, of higher purity, than the isocratic technique.

Furthermore, backwashing of the separating column also requires appreciable amounts of solvents, which cannot be recycled.

When in practice, also within the scope of preliminary tests, the user first develops, from columns with different stationary phases, the column with the most suitable stationary phase (such columns are supplied as test columns), optimization of the separation technique in practice is ultimately based on optimization of the mobile phase, namely through selection of the type of solvents, the pH value of the mobile phase, further additives etc., which then lead to improved separation.

It is simpler, however, to achieve defined selectivities by skillful selection of the correct stationary phase. A situation that often arises, however, is that as soon as separation is achieved between a particular critical pair of peaks, another pair of peaks merge into one peak elsewhere in the chromatogram.

To prevent this, it was proposed to use, as stationary phase, a mixture of suitable stationary phases (mixed bed), with which, for a specific separation problem in isocratic analysis, a selective separation can often be achieved.

G. J. Eppert and P. Heitmann proposed, in LC.GC Europe, p. 2, October 2003, optimization of mixed-bed columns based on first determining, using three or four test columns of different selectivity, the retention times of a test substance mixture, and then calculating a suitable mixed-bed column for the specific separation problem.

However, these stationary phases as mixed bed have the disadvantage that the column manufacturer must be commissioned to pack a corresponding mixed-bed column for each new separation problem. Thus, in the short term, the user is quite unable to carry out an isocratic analysis with the desired selectivity. The column cannot be packed by the user, who does not have the necessary special equipment, and lacks the relevant know-how. Moreover, it is also relatively difficult to pack a mixed bed in a separating column with good reproducibility.

It is known, from multidimensional chromatography, to provide columns branching from a main column, to be connected at different times, so that individual fractions are then "branched off" from the main column at a defined point of time via the temporarily connected column. Ultimately, separation of the mixture in multidimensional chromatography only takes place to a certain extent on the stationary phase of the separating device, and the main separation is achieved by switching to an additional separating device with an additional supply of eluent.

Even if good separations can be achieved with multidimensional chromatography, it is very expensive, fault-prone and is only suitable for routine measurements at considerable cost.

To solve special separation problems such as the separation of a 20-component amino acid mixture, J. L. Glajch et al. proposed, in "Journal of Chromatography", 318 (1985), page 23, improving the selectivity by combining stationary phases along with four mobile phases. However, this arrangement is based on purely empirical tests and has therefore not been calculated specifically.

For optimization of the mobile phase in liquid chromatography, Sz. Nyiredy, B. Meier, C. A. J. Erdelmeier, O, Sticher proposed, in "High Resolution Chromatogr. & Chromatogr. Communications" 8, (1985), the so-called "prism" model. In this, the solvent strength is plotted vertically, and the two-dimensional representation of the proportions of the components, which mainly influence the selectivity, is plotted in a horizontal plane.

Later, in column liquid chromatography, the overall optimum of the mobile phase was predicted from fifteen individual measurements and the local optimum of the mobile phase from twelve individual measurements (Sz. Nyiredy, W. Wosniok, H. Thiele, O. Sticher "Fluid Chromatogr." 14, 3077 (1991)).

This model was also employed for optimization of the extractants in liquid-liquid extraction, and in this case optimized extractants could be determined from twelve measured values (Sz. Nyiredy "Chromatographia" 51, 288 (2000)).

The present invention is based on the problem of providing a device and a method with which a chromatographic separation problem can be solved quickly, efficiently and in an environment-friendly manner with optimum selectivity and detectability.

This problem is solved by the features of claims 1 and 15.

According to the invention, a set of different separating elements is provided, from which a separating device with different stationary phases can be constructed, construction being carried out by coupling or connecting different separating elements together.

Said set according to the invention comprises separating elements of different stationary phases $S_i$ (i≥2) and at least three of these separating elements containing different stationary phases $S_i$, which can be coupled or connected together.

Coupling or connection is carried out by coupling or connecting the separating elements as such, in particular coupling the carrier elements, which form the separating element together with the respective stationary phase. For example, column segments can be coupled by coupling the column segments together on their respective tube ends.

Coupling of the separating elements via additional couplers or connectors is also possible.

Within the scope of the present invention, two stationary phases $S_A$ and $S_B$ are different if they differ from one another in their selectivity.

The minimal set thus comprises in each case three separating elements or column segments $S_A$ and in each case three separating elements or column segments $S_B$, where A and B are stationary phases of different selectivity.

Preferably, a set comprises at least three separating elements or column segments comprising different stationary phases $S_A$, $S_B$ and $S_C$, with the set containing of each of these kinds of separating elements, preferably at least 5, preferably at least 7 and especially preferably in each case 10 or more.

The respective stationary phases should be selected so that they possess different physiochemical properties.

Such a set can contain for example separating elements with stationary phases, comprising saturated or unsaturated alkyl groups (C1, C2, C3, C4, C6, C8, C12, C14, C16, C18, C22, C27, C30), which can be mono-, poly- or acyclic, ali- or heterocyclic, nitro, cyano, carbonyl, carboxyl, hydroxyl, diol, or thiol groups, glycidoxy groups, optionally etherified, amino or chiral groups, amide groups, carbamates, urea, perfluoralkyl groups or perfluoraryl groups and other haloalkyl and haloaryl groups, polybutadiene groups or other organic polymers, affinity-chromatographic modifications or ion-exchangeable groups (cation exchangers, anion exchangers, zwitterions), unmodified support materials (e.g. silica gel), molecularly imprinted polymers (MIPs) or combinations thereof, e.g. multifunctional stationary phases, optionally additionally to or instead of the aforementioned three different types of separating elements.

In contrast to multidimensional chromatography, the substances are separated on the separating device or column coupled or connected on the basis of optimization, i.e. the components of the mixture pass through the whole separating device. The separating elements that are coupled together remain connected to one another at least for a complete separation—a coupling or decoupling during the separation process, as is known in multidimensional chromatography, does not take place.

Another important point is that the ratio of the stationary phases of the coupled separating device to one another is variable, since the separating device can be dismantled again into the individual separating elements and a separating device with a different ratio of the stationary phases to one another and with a different selectivity can be constructed from them.

In contrast to the known mixed-bed columns, the desired column according to the invention is constructed by mechanical coupling of individual ready-to-use separating elements, i.e. generally by connecting or coupling together the carrier elements (e.g. pieces of tube as column segments). This does not alter the stationary phases that remain unchanged in the separating elements, in particular they are not mixed together.

In contrast to the production of pre-calculated mixed-bed columns, for which ultimately the column manufacturer packs a column according to specific customer requirements, i.e. has to prepare and mix a special stationary phase, according to the invention, the user can make the desired separating device in situ by simple mechanical coupling of the necessary column segments.

The invention also relates to a method of production of an optimized device for separating mixtures of substances.

First, with each of the at least two types of stationary phases $S_i$ (i≥2), a basis measurement of the mixture to be separated in a mobile phase that is to be established is carried out and the relevant retention factor k of each component is determined from (1)

$$k = (t_B - t_M)/(t_R - t_M^{Ec}) \quad (1)$$

($t_B$: retention time, $t_m$: flow time, $t_m^{Ec}$: extracolumn-volume-correction). The extracolumn-volume-correction takes account of the time contribution by the volume of the feed lines, of the injector and of the detector cell. It is recommended to specify the mobile phase so that the K values lie between the substances that are to be eluted first and last in the range from 1 to 20.

The basis measurement should preferably be performed on each kind of separating element (e.g. $S_A$, $S_B$, $S_C$) or on several similar or different coupled elements (for example 10 coupled elements $S_A$ or 5 $S_A$, 3 $S_B$, 2 $S_C$; 3 $S_A$, 5 $S_B$, 2 $S_C$ and 2 $S_A$, 3 $S_B$; 5 $S_B$). The basis measurement can also be carried out on a separate basis measurement column.

From the k values determined for each component to be separated and for each type of separating elements with the stationary phase $S_i$, the optimized combination of separating elements and their dimension is then calculated for the specific separation problem and the optimized separating device is then coupled or otherwise connected in the previously calculated manner from the separating elements of the predetermined dimension.

The dimension of a separating element means the volume of the respective stationary phase in the separating element. In the case of separating elements with a constant diameter the dimension is proportional to the length. If all separating elements have the same diameter and the same length, the dimension is proportional to the number N of separating elements to be coupled.

The most suitable combination of the separating elements for the specific separation problem is preferably calculated using the prism model. Preferably stipulating a predetermined number N of separating elements to be coupled, for any possible combination of stationary phases and their dimension, in particular the number of separating elements of a predetermined total number N=X+Y+Z of separating elements, based on the retention factors $k_i$ determined with the basis measurement, the respective retention factor of the component to be separated at selectivity point XYZ, i.e. the retention factor $k_{xyz}$ of the respective heterogeneous combination of the stationary phases $S_i$ is calculated $$k_{xyz} = (X \cdot k_A + Y \cdot k_B + Z \cdot k_C)/(X+Y+Z) \quad (2)$$

where X denotes the number of separating elements $S_A$, Y the number of separating elements $S_B$ and Z the respective number of separating elements $S_C$.

From the large number of calculated coupling possibilities XYZ, the coupling of the separating elements or segments with the best selectivity $\alpha$ is determined from $$\alpha = k_2/k_1 \quad (3)$$

or with the best resolution $R_S$ from $$R_S = 2 \cdot (t_{R2} - t_{R1})/(W_{1/2}1 + W_{1/2}2) \quad (4)$$

where $t_{R1}$ is the retention time of the respective compound and $W_{1/2}1$ is the half-height peak width of the respective compound, and the separating device, in particular column, optimized for this separation problem, and comprising N separating elements, is then coupled together from the respective elements or column segments.

With specially calculated coupling of the separating elements, in particular column segments, the stationary phase can be optimized with respect to the particular separation problem, so that it is no longer necessary to perform elution with a continuously or stepwise varying mobile phase or get the manufacturer to pack special mixed-bed columns.

If the basis measurement already shows that the desired separation can be achieved with only one type of column segments, the rest of the calculation can be used for optimizing the length of the column and for constructing the column only from the one type of column segments.

Otherwise the various possible combinations of the column segments for a given number of column segments N are calculated, until the desired separation is achieved. Optimization and calculation can be terminated when the desired selectivity $\alpha_{Crit}$ or resolution $R_{S,crit}$ of the critical peak pair or pairs is accomplished.

If, within the scope of calculation of the various possible combinations with for example three types of column segments and a total number of N column segments, sufficiently good separation is not calculated, i.e. no $R_{S,crit}$ is obtained below the value defined for the particular separation problem, the number N of column segments is altered, in particular increased, and the calculation is carried out once again with this altered number N'.

If, within the scope of this calculation with N column segments, no satisfactory separation is predicted, a new calculation becomes necessary, adding one or more additional stationary phases.

For this, basis measurements are carried out additionally with the additional column segments $S_j$ and then a new calculation is performed.

If, for a given combination, the separation capacity is insufficient, the resolution can be improved by increasing the total number of column segments N at the existing ratio. In practice, if separation is too good, the number of segments can be reduced in the same ratio, in order to shorten the total cycle time.

The separating device optimized for the particular separation problem is then coupled or connected from the separating elements in the calculated number and/or dimension and the corresponding separation is carried out.

The elution sequence and the resolution of the peaks can be predicted on the basis of the calculation.

Thus, the separating device, in particular column, optimized for the particular separation problem, can be assembled quickly and efficiently from the set of separating elements, namely generally on the basis of only three (!) basis measurements.

Although often three different stationary phases are sufficient to achieve a sufficiently effective, in particular isocratic separation, the number of stationary phases can of course be further increased to four, five or more, and the formula for calculating the heterogeneous retention factor K in the numerator and denominator is extended correspondingly to n stationary phases.

If the stationary phases or the separating elements comprising the stationary phases do not have the same dimensions (e.g. diameter and length of the packed column segments), the retention factor for each component can be calculated from the following equation $$K_{\alpha\beta\gamma} = (\alpha \cdot k_A + \beta \cdot k_B + \gamma \cdot k_C)/(\alpha+\beta+\gamma) \quad (5)$$

where $\alpha$, $\beta$, $\gamma$ correspond to the total internal volumes of the separating elements packed with the stationary phases A, B and C in the heterogeneous combination. $k_{A,B,C}$ are—as already described—the retention factors determined by the respective basis measurements.

If, in the subsequent measurement, a protective column must be provided before the separating device, this has to be taken into account in the basis measurement and in the calculation.

Another advantage is that the first column segment can also be regarded and used as a protective column and can if necessary be replaced very easily. Accordingly, use of an additional protective column is unnecessary.

The method according to the invention can moreover also be applied in a variant, so that—without stipulating particular dimensions of the separating elements—the optimized separating device is calculated from the basis measurements and the optimized column can then be packed correspondingly by the manufacturer according to the previously calculated proportions of the individual stationary phases. In this case the calculation provides the selectivity-optimized volumes of each stationary phase, and the individual volumes determined are then packed in a suitable carrier element, e.g. a suitable column.

Generally, with the device according to the invention and the method according to the invention, it is not the mobile phase that is subject to a continuously varying composition, but rather the separating device, in particular column, assembled separation-specifically by coupling the respective separating elements, has the varying composition that is necessary for a selective separation, based on separating elements or segments with different selectivities, i.e. the separating device has a gradient of the stationary phase.

Accordingly, separation with the device according to the invention can also take place isocratically with the desired selectivity, so that the disadvantages described for gradient elution are avoided. Thus, backwashing is not required, i.e. there is a saving of solvent and the total cycle time is shortened. In addition, the mobile phase or at any rate a large part of the fractions that are not contaminated with substances of different polarity in an isocratic elution, can be recycled, giving an additional saving on the costs for disposal and for the supply of fresh solvents, and it is also beneficial for the environment.

For this, preferably, individual regions of the mobile phase, which are laden with the respective separated substances, are removed and the rest of the solvent is captured, recycled and reused. Especially in the area of preparative chromatography, which uses considerable amounts of solvents, reusability of the solvents achieved with isocratic chromatography is not only of great advantage on environmental grounds, but also represents a considerable cost saving, as the costs of disposal and supply of fresh solvents are greatly reduced.

Another important advantage of the invention is that, with isocratic elution, many more different detection principles and therefore detectors can be used for determining the respective substances.

Since the composition of the mobile phase remains constant in isocratic elution, the differential refractometer can again be used for universal detection of the substances.

Often, the isocratic elution of the substances and therefore the separation with the set according to the invention can take place in an acetonitrile/water mixture, for which the rise in absorption in the UV does not begin until a wavelength of 190 nm (50% transmission). Accordingly, substances with chromophores can, as a result of isocratic elution, be detected even in the short-wave UV region.

The separation that can be carried out isocratically according to the invention thus makes it possible to use other, often more suitable, more sensitive and/or less expensive methods of detection.

As the composition of the mobile phase is constant over time, in addition of course, in each method of detection the base line is more stable and effects due to mixing are avoided.

Isocratic separation also has a beneficial effect on the quality of the mass spectra, as the ionization remains constant and in addition no gradient-induced secondary effects occur (stable, constant background).

Moreover, for detection in isocratic elution it is also possible to use electrochemical detectors or conductivity detectors.

Since, as a result of isocratic analysis, nearly all detection principles are now available, there is the possibility of coupling the various detectors in series, for improved characterization of the substances.

Furthermore, with the device according to the invention, the fault-prone equipment required for providing the gradient, such as additional pumps and gradient mixers, is no longer required, leading not only to lower acquisition costs for the chromatograph, but also to reduced operating costs.

The set of separating elements according to the invention and the method according to the invention can be used for all methods employing physicochemical separation based on different interactions with at least two phases, such as gas chromatography (GC), liquid chromatography (LC) (column or planar), chromatography with supercritical gases as the mobile phase (supercritical fluid chromatography, SFC), electrophoretic separation techniques, in each case in the nano, micro, analytical and preparative areas of application, and in the area of sample preparation and/or purification by solid-phase extraction or filtration.

In liquid chromatography, methods are also employed that take place at reduced pressure (e.g. flash chromatography) or elevated pressure (e.g. HPLC, MPLC) or that utilize different mechanisms of interaction for separation, e.g. reversed-phase liquid chromatography (RP), normal-phase chromatography (NP), ion chromatography (IC), size-exclusion chromatography (SEC, GPC) or hydrophobic interaction chromatography (HIC, HILIC).

The separating element of the stationary phase can be for example a segment of a column, a segment of a TLC plate or of an electrophoresis gel. Although the present invention is described mainly with reference to columns and column segments, what is said also applies appropriately to other separating elements or segmented or segmentable separating devices, for example TLC plates, which can be adapted to any possible length of the stationary phase in question.

The coupling of stationary phases is also independent of the type of support material used (silica gels, polymers, metal oxides, glasses, quartz glasses, polysaccharides, agarose gels, carbon etc.) and also applies to all orders of magnitude of the chromatographic process, from miniaturized nano-methods to the preparative range.

Furthermore, the stationary phase can be either particulate, fibrous or fiberlike, or it can be monolithic. An advantage in using monolithic stationary phases is that they can be coupled very easily, as the stationary phase does not have to be retained by frits or sieves.

The present invention is also especially advantageous when used in nanotechnology, because with such small amounts it is extremely difficult to provide gradients in the mobile phase reproducibly.

Of course, the set according to the invention can also be adapted to special separation techniques or can contain special segments for special separation problems, if necessary as additional segments.

Thus, in ion chromatography or ion-pair chromatography it is also possible to construct the stationary phase from column segments or for example also couple the column segments for ion-pair chromatography with other column segments, for example polar column segments.

A further advantage of using specially pre-calculated and then coupled or assembled separating devices is shortening of the total cycle time. The use of the separating elements and calculation of the individual separating elements that are to be coupled together as well as their number ultimately also permits optimization of the total cycle time, i.e. as short as possible, but long enough to achieve the desired separation.

A set can also comprise segments for targeted adsorption of certain substances, as in solid-phase extraction. From the mixture that is to be separated, the substance in question is adsorbed almost quantitatively in this specific adsorption segment and is thus enriched in this segment, and is then desorbed again. Instead of only in one segment, as customary until now, a veritable cascade of segments could be envisaged for targeted adsorption of different substances in series.

The segments according to the invention can also be used in other separation techniques, such as in electrochromatography, in which mixtures of substances are separated on the basis of electroosmotic flow, or in electrophoresis.

The set according to the invention and the method according to the invention are suitable for continuously-operating online processes and/or methods of separation with a mobile phase and/or constant rate, for example HPLC, online-TLC and online-OPLC.

The set according to the invention can also comprise at least two different types of TLC-plates, which should then each be contained in the set in a larger number, in particular at least three of each kind. The TLC-plates can be adapted to the optimized length and the various TLC-plate segments can then be coupled together to a plate formed from the various segments and therefore ultimately a plate with a gradient in the stationary phase.

In particular, the set enables users to construct in situ a separating device that is especially suitable for their (routine) analysis, and then separation can take place with the advantages of isocratic elution already described.

The advantages of the optimized separating device are achieved in particular when the separating device, once optimized, is used in the continuous separation process, namely isocratically and with a constant stationary phase throughout the separation, i.e. even without "switching" the columns.

In particular applications it is also possible of course, in addition to optimization of the stationary phase, to optimize the mobile phase as well for the separation in question, for example also with a gradient.

The specific design of the particular column segments depends of course on the type of separating technique and the amounts of substances to be separated using the separating device prepared from the separating elements that are to be coupled together.

The length of each individual separating element depends on the subsequent total length of the device comprising the stationary phase, in particular the column, and the desired number of segments and the specific separation problem. In the case of separating elements that are segments of analytical LC columns, the length of a segment is at least 0.5 cm, preferably at least 1.0 cm, to provide simple mechanical coupling-together of the segments. The length of a column segment is preferably 2 cm, so that a column with a length of 20 cm can be constructed from 10 coupled segments. Especially preferably, the length of a column segment is 1 cm or an integral multiple thereof and can be up to 500 cm; preferably the length of a column segment is not more than 12.5 cm. In capillary gas chromatography (cGC), column segment lengths up to 100 m can be envisaged, and the length is preferably 25 m.

The column segments can have either the shape of a straight cylinder or of a spiral cylinder (especially in the case of long column segments, for example for GC) or can be of some other shape.

The inside diameter of the column varies considerably depending on the amount of substance to be separated and the particular chromatographic process and can be between about 20 µm and 2 m, in the case of an analytical column generally between 20 µm and 10 mm. For isolation purposes a column with an inside diameter between 2 mm and 1 m will be used.

It is in principle also possible for the set to comprise additionally "multiple segments". These "multiple segments" are column segments of a defined stationary phase also present in the "single segment", but the length of the "multiple segment" is an integral multiple of the length of an individual segment. For example, in addition to 10 individual segments with a phase comprising phenyl groups of length 2 cm, the set can also contain a "double segment" with a phase comprising phenyl groups of length 4 cm and a triple segment with the phase comprising phenyl groups of length 6 cm, and with these multiple segments that are additionally present, the time required for coupling together and dismantling the segments can be reduced.

Theoretical considerations based on the prism model show that, when in addition to column segments of length l in each case a column segment of each type of stationary phase with a smallest possible length (e.g. ½ or ¼) is included in the calculation, a far wider working range for selectivity optimization can be covered with a reasonable number of calculations, than if for example the total number N of column segments were to be increased overall by one or two segments.

The separating elements should be coupled by means of connections that are inert and free from dead space as far as possible, for example by means of
  capillary joints
  directly with the aid of a coupler with small dead space
  in the case of capillary columns, by joining the ends of the capillaries using a coupler, with the ends of the capillaries being butted together directly
  again in the case of capillary columns, by shrink-fitting the ends of the capillaries via a shrinkable sleeve
  by screwing the column ends together using a gasket with a through-hole
  via a screw connection with a capillary hole
  directly by bringing together the packing end of one separating element with the packing end of another separating element
  by segmented packing of the stationary phase in a column tube Preferably, each separating element has the same coupling means at each end, so that any end of one column segment can be connected to any end of another column segment.

Another preferred embodiment envisages providing coupling means that are different from one another (male, female) at either end of the column segment. In this case the end of one column segment is inserted in the start of the next one, maintaining the inside diameter of the packing cross-section and therefore keeping the linear flow rate constant. In this way, no turbulence develops at the coupling points. Other advantages of this system are the chambered seal at the coupling points and the protected packing of the individual separating elements. Moreover, the packing is closed internally and protected. The simple manipulation by inserting in one another is especially advantageous. However, the most important point with this coupling is that coupling is virtually free of dead space, since the end of the separating segment is pressed directly, with a thin frit, onto a sieve with desired cross-filtration.

It is also possible to provide a monolithic seal, with thickness preferably between 0.5 and 1 mm, at either end of a column segment. These column segments are coupled similarly to the manner described above (male, female). In this case there is the advantage that it is not necessary to use any metallic terminations such as sieve and frit. Furthermore, the monolithic seal can be modified chemically and can thus be adapted to the particular stationary phase used. With this system it is possible for two separating elements to be connected together without a transition element (such as sieve and frit).

If chromatographic plates shortened to the appropriate length (dimension) are used as separating elements, for example in TLC, OPLC or HPTLC, the separating elements can be coupled by overlapping the stationary phases of two plates at the plate ends, so that the stationary phase of the first plate for example is directed upward and the stationary phase of the next plate is directed downward and so on, or the plates are placed next to each other and then coupled via an inert bridge, which then overlaps the stationary phases of both plates.

The method according to the invention will now be explained in more detail with an example of application.

I. Example of Calculation of the Optimized Combination of the Separating Elements (Column Segments) in Question on the Basis of the Prism Model:

a) For a mixture of methylparaben, acetophenone, ethylparaben, dimethyl phthalate, 2,3-dimethylphenol, methyl benzoate and anisole, determine the best possible separation that is possible with a combination of 10 column segments with cyano and/or phenyl and/or C18 groups in acetonitrile/water 30:70 (v/v) as solvent.

The set comprises in each case at least 10 column segments with CN as stationary phase ($S_{CN}$), 10 column segments with phenyl groups as stationary phase $S_{PH}$ and 10 column segments with C18 as stationary phase ($S_{C18}$)

For each of these three different stationary phases, the respective retention factor k, shown in the following table, is determined according to (1) within the scope of a basis measurement for each of the 7 different substances to be separated:

|   | Component | $k_{CN}$ | $k_{PH}$ | $k_{C18}$ |
|---|---|---|---|---|
| 1 | Methylparaben | 2.4 | 5.0 | 10.2 |
| 2 | Acetophenone | 2.8 | 7.0 | 8.6 |
| 3 | Ethylparaben | 3.1 | 7.7 | 20.1 |
| 4 | Dimethyl phthalate | 3.2 | 9.6 | 10.5 |
| 5 | 2,3-Dimethylphenol | 3.5 | 9.7 | 26.3 |
| 6 | Methyl benzoate | 3.5 | 11.0 | 17.2 |
| 7 | Anisole | 3.7 | 11.8 | 19.0 |

In the present example, the total number of column segments N to be coupled together is set at 10. For each heterogeneous coupling of the column segments, i.e. X-times the stationary phase $S_{CN}$, Y-times the stationary phase $S_{PH}$ and Z-times the stationary phase $S_{C18}$ with N=10=X+Y+Z, the retention factor $$k_{xyz}=(X*k_{CN}+Y*k_{PH}+Z*k_{C18})/(X+Y+Z) \quad (6)$$

of the heterogeneous coupling at the selectivity point XYZ is calculated according to (2). The selectivities of all adjacent pairs of peaks are now calculated from the calculated retention factors of the respective couplings XYZ of separating elements. The optimum selectivity point is the point XYZ at which all pairs of peaks achieve a base line separation. If several selectivity points achieve a base line separation, the ideal point is the one with additionally the smallest retention factor for the last eluting component.

The value for the base line separation, the point at which a peak reaches the base line again, depends on the particular chromatographic technique or on the separation efficiency that the particular method of separation can achieve. In the case of HPLC, to satisfy the requirements for good resolution, this value should be about 1.15, for GC it should be about 1.05 and for TLC it should be greater than 1.3.

As shown by the following comparison of measured and calculated retention factors for the example of the selectivity point 442, i.e. 4 segments $S_{CN}$, 4 segments $S_{PH}$ and 2 segments $S_{C18}$, the average deviation between calculated and measured retention factors is on average approx. 4%:

|  | 1 | 2 | 3 | 4 | 5 | 6 | 7 |
|---|---|---|---|---|---|---|---|
| $k_{measured}$ | 6.59 | 7.01 | 9.04 | 11.77 | 12.22 | 13.29 | 15.11 |
| $k_{calculated}$ | 6.31 | 6.86 | 8.80 | 11.07 | 11.81 | 12.82 | 14.21 |
| Deviation [%] | 4.5 | 2.2 | 2.7 | 6.3 | 3.5 | 3.6 | 6.3 |

The selectivity of a separation depends on, among other things, how many separating elements or column segments with different stationary phases (or different polarity of the latter) can be coupled together and on the total number N of column segments to be coupled.

a2) For a Mixture of 8 Triazines, Determine the Best Possible Separation that is Possible with a Combination of in Each Case 10 Column Segments with Cyano and/or Phenyl and/or C18 Groups and/or C18 with Polar Embedded Amide Group in Methanol/Water 50:50 (v/v) as Solvent.

The set comprises in each case at least 10 column segments with CN as stationary phase ($S_{CN}$), 10 column segments with phenyl groups as stationary phase $S_{PH}$, 10 column segments with C18 as stationary phase ($S_{C18}$) and column segments with polar embedded C18 as stationary phase ($S_{peC18}$).

For each of these four different stationary phases, within the scope of a basis measurement, the respective retention factor k is determined according to (1) for each of the 8 different substances to be separated, and is shown in the following table:

|   | Component | $k_{CN}$ | $k_{PH}$ | $k_{C18}$ | $k_{peC18}$ |
|---|---|---|---|---|---|
| 1 | Prometone | 1.16 | 4.57 | 6.09 | 4.51 |
| 2 | Simetryn | 1.28 | 6.82 | 11.85 | 7.55 |
| 3 | Ametryn | 1.41 | 7.73 | 12.18 | 7.42 |
| 4 | Prometryn | 1.45 | 10.41 | 22.82 | 14.19 |
| 5 | Terbutryn | 1.39 | 10.15 | 19.70 | 11.16 |
| 6 | Simazine | 1.61 | 11.85 | 24.03 | 15.72 |
| 7 | Atrazine | 1.78 | 18.57 | 46.50 | 27.22 |
| 8 | Propazine | 1.97 | 21.69 | 55.86 | 27.85 |

Figure 5:
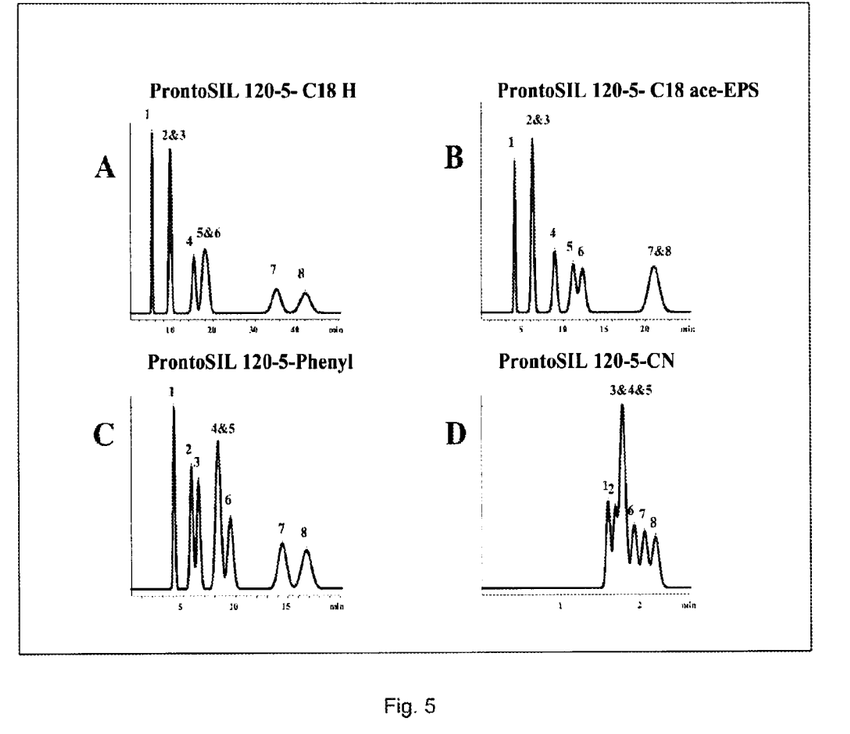
FIG. 5: a set of chromatograms that shows the separation of triazines on different stationary phases.

The chromatograms for these values are shown in FIG. 5. It can be seen that none of the individual separating columns is able to solve the separation problem by itself.

The optimum composition of the stationary phase can be determined from the calculation of the k values and selectivities of all possible combinations. In this case it comprises 180 mm of the phenyl phase, 60 mm of the C18 phase with polar embedded group and 60 mm of the cyano phase.

The retention factors calculated for the optimum column composition are compared against the measured values in the following table. The deviations are on average 3.4%.

|  | 1 | 2 | 3 | 4 | 5 | 6 | 7 | 8 |
|---|---|---|---|---|---|---|---|---|
| $k_{measured}$ | 4.30 | 6.42 | 6.90 | 9.09 | 9.96 | 10.75 | 17.21 | 20.19 |
| $K_{calculated}$ | 4.30 | 6.47 | 7.06 | 9.45 | 10.29 | 11.60 | 18.52 | 20.74 |
| Deviation [%] | 0.0 | 0.8 | 2.3 | 3.8 | 3.2 | 7.3 | 7.1 | 2.7 |

Figure 6:
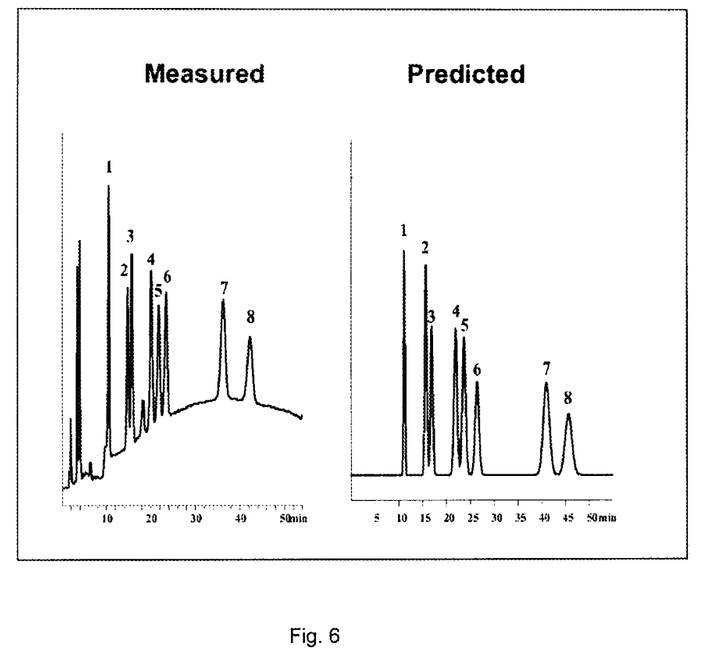
FIG. 6: measured and predicted chromatograms for the separation of triazines.

The calculated and measured chromatograms are compared in FIG. 6. It can clearly be seen that they are in excellent agreement.

b) Number of Possible Combinations

I) Starting from s=3 different column segments ($S_A$, $S_B$ and $S_C$; here: $S_{CN}$, $S_{PH}$ and $S_{C18}$) of the same dimension and a total number N=10 of coupled column segments, we get 27 possible combinations, if only two of the three different column segments are coupled together, i.e. only $S_A$, $S_B$ or $S_A$, $S_C$ or $S_B$, $S_C$. There are an additional 36 possible combinations if all three different column segments $S_A$, $S_B$, $S_C$ are coupled together.

Thus, in total, with three types of column segments of different polarity and a total number of 10 segments to be coupled, there are 63 possible combinations.

II) If the number of columns to be combined is not given as exactly 10, but instead the total number N is given as a range from 6 to 15, with n=6 to 15, s=3 the number of possible combinations increases to 625.

III) The use of an additional stationary phase $S_D$, i.e. s=4, for the above calculation of the possible combinations (I), i.e. N=10, with three stationary phases gives 960 possible combinations with 2, 3 or 4 stationary phases.

IV) If, on the basis of III), the total number is extended to at least 6 and at most 15, then with s=4 and the combinations of in each case 3 phases we get a total of 2500 possibilities.

By extending the number of available stationary phases for example to five or more, of combinations with one another (for example combinations not more than three, but of four different stationary phases in coupling), there is a further increase in possible combinations.

Further "fine-tuning" can be achieved by taking into account ½ or ¼ segments in the calculation.

The invention is described below on the basis of a preferred example of application for the coupling of the column segments.

The column comprises one or more column segments and a holder, which in its turn comprises individual holding elements that can be screwed together, and can if required be screwed to the connectors at the top and bottom of the respective column.

Independently of this especially preferred embodiment described in detail below, it is also possible for the individual holding elements to be connected by means of bayonet joints or other types of joints. Moreover, it is also possible to omit individual holding elements entirely and insert the column segments into a guide sleeve of the appropriate length with threaded ends, and then press together the individual column segments axially with the connectors that can be screwed on the guide sleeve.

The column segments can also be pressed together axially by hydraulic means in an appropriate device.

An important point in the following especially preferred embodiment is that the inside diameter of the column remains constant even at the coupling points so that the flow rate is constant throughout the column.

Furthermore, the column coupling described below can also be used in general for the coupling of columns, for example of precolumns and main columns.

BRIEF DESCRIPTION OF THE DRAWINGS

The diagrams show:

FIG. 1: a) an exploded view of a column segment and b) a schematic representation of the complete column segment.

DESCRIPTION OF THE PREFERRED EMBODIMENTS

Figure 1A:
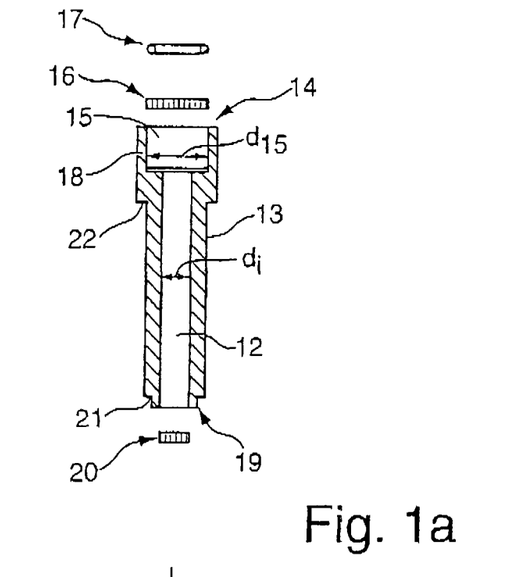
Figure 1B:
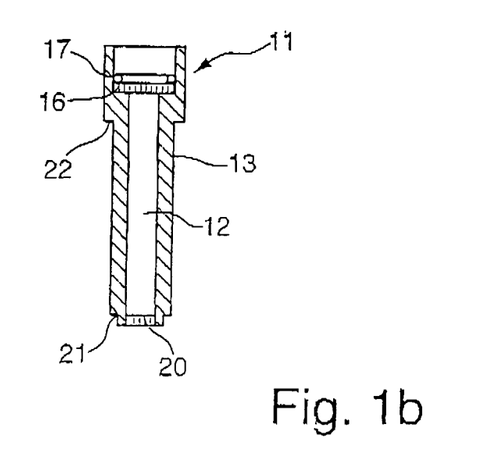

The column segment 11 (cf. FIG. 1) comprises a column tube 13 with a stationary phase 12. The column tube 13, which can be made for example of metal, plastic, ceramic or combinations thereof, has a predefined outside contour with steps 22, 21 and a constant inside diameter $d_i$.

At the head end 14, the tube 13 is provided with a defined recess 15, which must be larger in diameter $d_{15}$ than the inside diameter $d_i$. The recess 15 has a shoulder, for the fitting seal 17. The seal 17 can be made for example of plastic, metal or some other material suitable for sealing. The recess 15 receives a filter or a filter-sieve combination 16, which protects the stationary phase, and has the ring seal 17 above it. The wall 18 of the recess 15 serves simultaneously as a guide during coupling with another column segment 11' or for fitting a male adapter 40, described later.

The tube 13 is shaped at its foot 19 according to a male connector 21 and is closed by a porous frit 20, which has the purpose of holding the stationary phase 12 in the tube 13. The porous frit 20 can be of metal, plastic, ceramic, sintered silica gel, monolithic silica gel or monolithic polymer, optionally surface-modified.

The holding element 30 (FIG. 2) receives the column segment 11 and its coupling. The holding element 30 can be of metal, plastic, ceramic or a combination thereof. It has an internal thread 32 at the head end 31 and an external thread 34 at the foot end 33. Inside the holding element 30 there is a through-hole 35 with a step 36, into which the column segment 11 fits. The step 22 of the column segment 11 bears on the step 36 of the holding element 30.

Figure 2:
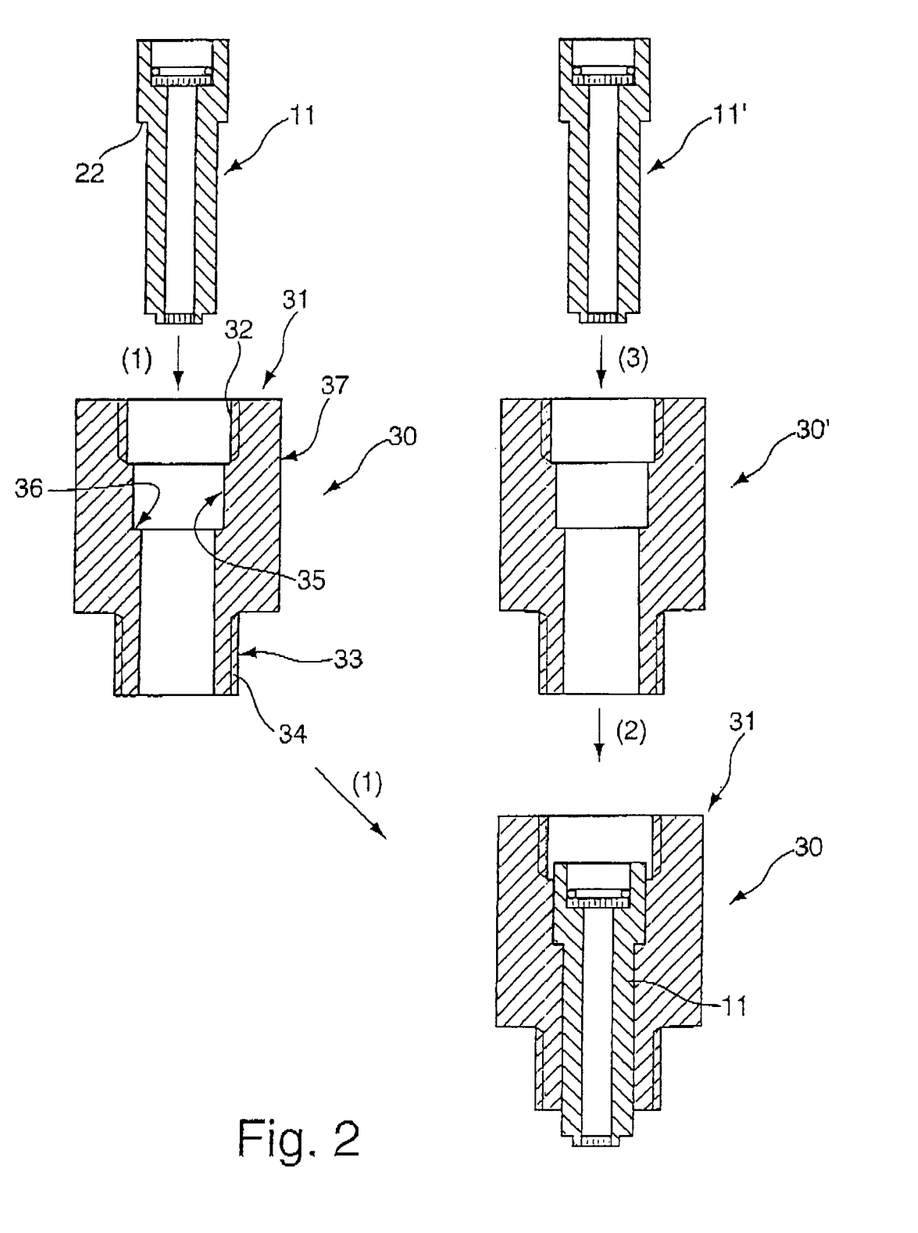
FIG. 2: a schematic representation of the fitting of a column segment from FIG. 1 b) in a holding element 30 (Step 1), the fitting of a further holding element 30' (Step 2) and the fitting of a further column segment 11' (Step 3)

The outside surface 37 of the holding element 30 can be knurled diagonally or axially for easier manipulation or can have surfaces for using a wrench.

Figure 3:
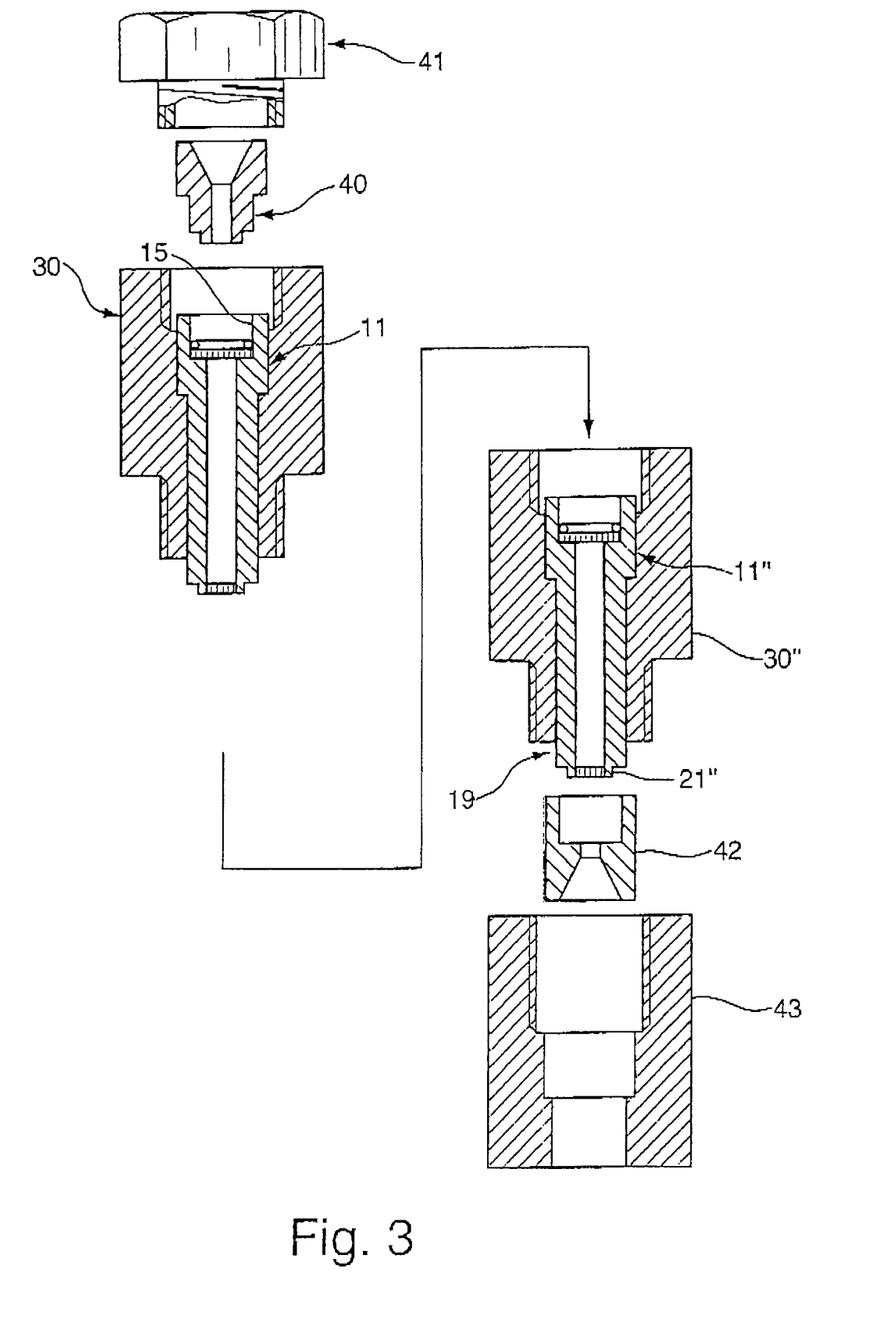
FIG. 3: a schematic representation of the coupling of the top column segment 11 or of the top holding element 30 and of the bottom column segment 11'' or of the bottom holding element 30'' to the respective adapters
Figure 4:
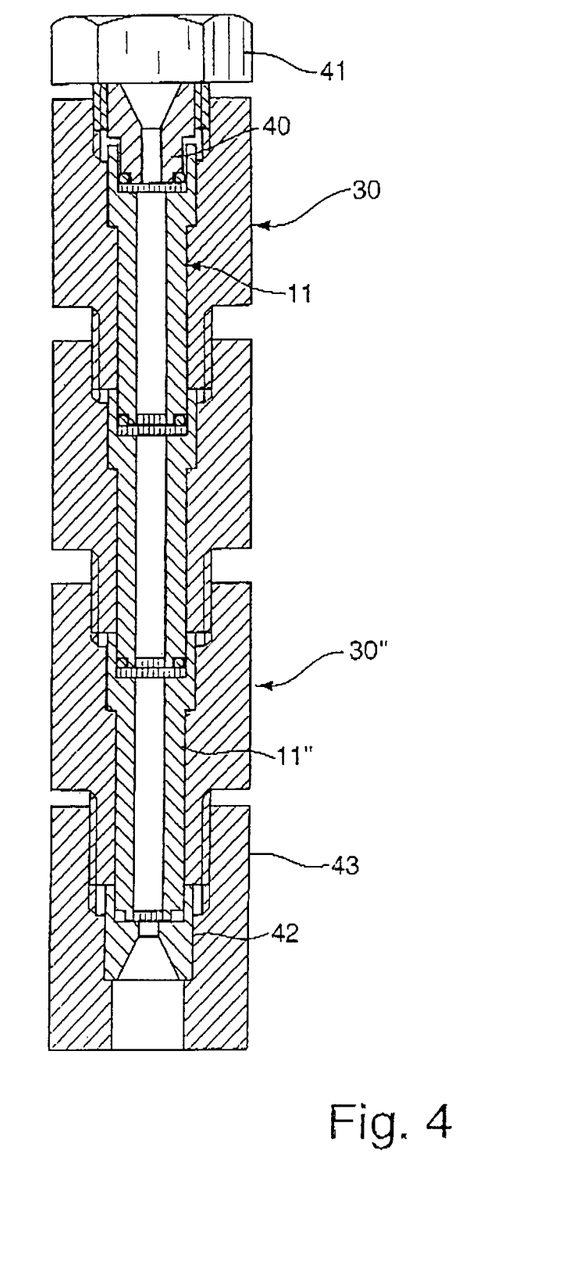
FIG. 4: a schematic representation of the column segments and adapters coupled together to form a column.

Assembly of the column segments is illustrated in FIGS. 2 and 3:
1. Put the column segment 11 in the holding element 30 in the manner described previously (arrow 1 in FIG. 2).
2. Screw another holding element 30' fully into the first holding element 30 at the head end 31. This locks the column element 11 in the holding element 30 (arrow 2 in FIG. 2).

3. Put another column segment 11' into the threaded holding element 30' (arrow 3 in FIG. 2).
4. Repeat steps 2 and 3 until the desired number of column segments 30 is reached.
5. Insert a male adapter 40 into the recess 15 in the top column segment 11 in FIG. 3 and screw the adapter screw 41 into the holding element 30.
6. At the bottom end 19 of the bottom column segment 11", fit the female adapter 42 on the projection 21" and screw on the holding element 30 with the adapter nut 43.
7. The resultant segmented column can now be connected by means of a capillary connection (stainless steel, plastic or fused silica) to the chromatographic system.

If, in the above preferred embodiment, for example a double-length column segment is to be connected to other column segments, the double-length column segment can be held in two holding elements joined together and can then be coupled.

The invention claimed is:

1. A set of elements for the production of a device for separating substances by distributing between a stationary and a mobile phase, wherein the set includes at least six individual separating elements, wherein each of the at least six individual separating elements is a column segment comprising a carrier element, a stationary phase secured within the carrier element, and coupling means, wherein the stationary phase of at least three of the separating elements is a first stationary phase and the stationary phase of at least three of the separating elements is a second stationary phase, the second stationary phase differing from the first stationary phase, wherein each of the separating elements can be coupled to any of the other separating elements and thereafter can be disconnected therefrom in such a way as to permit reuse of the disconnected separating elements with their respective stationary phases, and wherein the set can be used by the user on site to produce a desired separating device by simply coupling the necessary column segments together mechanically.

2. The set as claimed in claim 1, characterized in that the coupling or connecting of the separating elements together is carried out by coupling or connecting the carrier elements.

3. The set as claimed in claim 1, characterized in that the set comprises separating elements with at least three stationary phases of different selectivities $S_A$, $S_B$ and $S_C$ and of each of these three types of separating elements, at least 3, preferably at least 5, preferably at least 7, and especially preferably 10 or more are contained in the set.

4. The set as claimed in claim 1, characterized in that the stationary phases of the set are selected from the group comprising the saturated or unsaturated alkyl groups (C1, C2, C3, C4, C6, C8, C12, C14, C16, C18, C22, C27, C30), which can be mono-, poly- or acyclic, ali- or heterocyclic, nitro, cyano, carbonyl, carboxyl, hydroxyl, diol, or thiol groups, glycidoxy groups, optionally etherified, amino or chiral groups, amide groups, carbamates, urea, perfluoralkyl groups or perfluoraryl groups and other haloalkyl and haloaryl groups, polybutadiene groups or other organic polymers, affinity-chromatographic modifications or ion-exchangeable groups (cation exchangers, anion exchangers, zwitterions), unmodified support materials (e.g. silica gel) and molecularly imprinted polymers (MIPs).

5. The set as claimed in claim 1, characterized in that the length of a separating element, in particular a column segment, is between 0.5 cm and 50 m, preferably between 1.0 and 12.5 cm and especially preferably between 1.5 and 2.5 cm.

6. The set as claimed in claim 1, characterized in that the set additionally comprises separating elements or separating devices for carrying out a reference measurement, with the number of separating elements or separating devices for carrying out the reference measurement preferably corresponding to at least the number of separating elements $T_i$ of different stationary phases $S_i$ contained in the set.

7. The set as claimed in claim 1, characterized in that the set also comprises multiple segments or multiple elements, the length or dimension of which corresponds to a multiple of the length or dimension of a single separating element.

\* \* \* \* \*